US009965849B2

(12) United States Patent
Suzuki et al.

(10) Patent No.: US 9,965,849 B2
(45) Date of Patent: May 8, 2018

(54) VOID EVALUATION APPARATUS AND VOID EVALUATION METHOD IN THE SOLDER

(71) Applicants: OSAKA UNIVERSITY, Osaka (JP); BEAMSENSE Co., Ltd., Osaka (JP)

(72) Inventors: Takashi Suzuki, Osaka (JP); Sueki Baba, Osaka (JP)

(73) Assignees: OSAKA UNIVERSITY, Osaka (JP); BEAMSENSE Co., Ltd., Osaka (JP)

( * ) Notice: Subject to any disclaimer, the term of this patent is extended or adjusted under 35 U.S.C. 154(b) by 92 days.

(21) Appl. No.: 15/034,302

(22) PCT Filed: Nov. 10, 2014

(86) PCT No.: PCT/JP2014/079717
§ 371 (c)(1),
(2) Date: May 4, 2016

(87) PCT Pub. No.: WO2015/072424
PCT Pub. Date: May 21, 2015

(65) Prior Publication Data
US 2016/0267646 A1    Sep. 15, 2016

(30) Foreign Application Priority Data
Nov. 15, 2013    (JP) .................................. 2013-237024

(51) Int. Cl.
*G06K 9/00*    (2006.01)
*G06T 7/00*    (2017.01)
(Continued)

(52) U.S. Cl.
CPC ........... *G06T 7/0008* (2013.01); *G01N 23/04* (2013.01); *H05K 3/3436* (2013.01);
(Continued)

(58) Field of Classification Search
CPC ......... G06T 7/0008; G06T 2207/10116; G06T 2207/30152; G06T 2207/30164;
(Continued)

(56) References Cited

U.S. PATENT DOCUMENTS

| 2011/0081070 A1* | 4/2011 | Yamamoto | G06T 5/50 382/145 |
| 2011/0255768 A1* | 10/2011 | McElfresh | G06T 7/001 382/141 |
| 2016/0148899 A1* | 5/2016 | Ichimura | H01L 24/81 361/767 |

FOREIGN PATENT DOCUMENTS

| JP | 2004-198206 A | 7/2004 |
| JP | 2004198206 A * | 7/2004 |

(Continued)

OTHER PUBLICATIONS

International Search Report dated Feb. 10, 2015 in corresponding Japanese Application No. PCT/JP2014/079717; 1 pg.
(Continued)

*Primary Examiner* — Jonathan S Lee
(74) *Attorney, Agent, or Firm* — Maier & Maier, PLLC

(57) ABSTRACT

A void evaluation apparatus in a solder includes an evaluation function calculation unit for calculating a solder evaluation function by using a pixel value pi contained in the voids that is set to 1 and the pixel value pi not contained in the voids is 0 for each pixel constituting an image in the solder, and by using a weight function w(ri), which is maximum at a solder center (ri=0), and is 0 at a maximum radius (ri=r0) for a distance ri from the solder center. The apparatus further has a void evaluation unit for evaluating that the influence of voids is larger as the evaluation function is relatively larger for the each solder.

(Continued)

$$\frac{\sum_{i=1}^{N} w(r_i) p_i}{\sum_{i=1}^{N} w(r_i)} \times 100$$

i: pixel number (1–N)
pi: pixel value (0 or 1)
w(ri): weighting function

9 Claims, 10 Drawing Sheets

(51) Int. Cl.
*G01N 23/04* (2018.01)
*H05K 3/34* (2006.01)

(52) U.S. Cl.
CPC .......... *G01N 2223/401* (2013.01); *G01N 2223/6113* (2013.01); *G01N 2223/648* (2013.01); *G06T 2207/10116* (2013.01); *G06T 2207/30152* (2013.01); *G06T 2207/30164* (2013.01); *H05K 2201/10734* (2013.01); *H05K 2203/162* (2013.01); *H05K 2203/163* (2013.01); *Y02P 70/613* (2015.11)

(58) Field of Classification Search
CPC ............ G01N 23/04; G01N 2223/401; G01N 2223/648; H05K 3/3436; H05K 2201/10734; H05K 2203/162; H05K 2203/163; Y02P 70/613
See application file for complete search history.

(56) References Cited

FOREIGN PATENT DOCUMENTS

JP  2006-226875 A  8/2006
JP  2007-121082 A  5/2007

OTHER PUBLICATIONS

Asaad F. Said et al., "Robust Automatic Void Detection in Solder Balls", ICASSP 2010, p. 1650-1653, IEEE International Conference on IEEE, 2010, 4 pgs.
Shao-hu Peng, Hyun Do Nam, "Void defect detection in ball grid array X-ray images using a new blob filter", Journal of Zhejiang University—Science C, 2012, p. 840-849, 10 pgs.
Notification of Transmittal of Translation of the International Preliminary Report on Patentability dated May 26, 2016, in connection with corresponding PCT Application No. PCT/JP2014/079717 (7 pgs).

\* cited by examiner

VOID EVALUATION APPARATUS AND VOID EVALUATION METHOD IN THE SOLDER

TECHNICAL FIELD

The present invention relates to an evaluation (assessment) apparatus of voids in solder and an evaluation (assessment) method of voids in solder.

BACKGROUND ART

Japanese Laid-open Patent Application Publication No. 2006-226875 discloses a method of detecting a bonding defect of a solder ball by X-ray. In this method, the bonding defect of the solder ball is evaluated by an area, flatness and the like.

In recent years, automatic detection techniques of voids have been developed as a performance evaluation of a BGA (Ball Grid Array). These use statistical procedures as a principle of operation.

For example the number of voids and a ratio of the void area to the solder ball are used as the index indicating the reliability of the solder ball, as detailed in Non-Patent Documents 1 and 2.

RELATED ART DOCUMENTS

Patent Document

Patent Document 1
JP A-2006-226875
Non-Patent Document 1
Said, Asaad F., et al. "Robust automatic void detection in solder balls", Acoustics Speech and Signal Processing (ICASSP), 2010, IEEE International Conference on IEEE, 2010
Non-Patent Document 2
Peng, Shao-hu, and Hyun Do Nam, "Void defect detection in ball grid array X-ray images using a new blob filter", Journal of Zhejiang University Science C13.11 (2012), 840-849

SUMMARY OF THE INVENTION

Problems to be Solved by Invention

However, the following problems are pointed out in the above methods. First, one problem is that only the number of voids and the ratio of the void area to the solder ball are used as the index indicating the reliability of the solder balls. Certainly, because increases of the number of voids lead to a bad connection of BGA and increases of the ratio of the void area to the solder ball lead to a poor connection of BGA, they may be an indicator of evaluation. However, the present inventors found that it is insufficient to determine an indicator of evaluation only by the number of voids and the ratio of the void area to the solder ball, and that it is more important for voids to be existed in any position for BGA. In particular, the present inventors found that the effect on joint strength becomes large as the void is located in the center of the solder ball.

Another problem is an evaluation speed. In the conventional method it takes a very long time to calculate. Because the number of solder balls per package may exceed 1000, it is not preferable to take a lot of time for evaluation.

Thus it is for an object of the present invention to provide the evaluation apparatus and the method of evaluating voids in the solder, wherein the voids in the solder can be evaluated at a high speed and more precisely.

Means for Solving the Problems

A void evaluation apparatus in a solder according to the present invention includes:

an evaluation function calculation unit for calculating a solder evaluation function as shown the following, by using that a pixel value pi contained in the voids is set to 1 and the pixel value pi not contained in the voids is 0 for each pixel constituting an image in the solder, and by using a weight function w(ri), which is maximum at a solder center (ri=0) and is 0 at a maximum radius (ri=r0) for a distance ri from the solder center; and a void evaluation unit for evaluating that the influence of void is larger as the evaluation function is relatively larger for the each solder.

$$\frac{\sum_{i=1}^{N} w(r_i) p_i}{\sum_{i=1}^{N} w(r_i)} \times 100$$

i: pixel number (1–N)
pi: pixel value (0 or 1)
w(ri): weighting function

Effect Of the Invention

According to the void evaluation method in the solder concerning the present invention, the voids in each solder can be evaluated at a high speed and accurately.

FORM FOR INVENTION TO BE PERFORMED

A void evaluation apparatus in a solder according to first aspect includes:

an evaluation function calculation unit for calculating a void evaluation function as shown the following, by using that a pixel value pi contained in the voids is set to 1 and the pixel value pi not contained in the voids is 0 for each pixel constituting an image in the solder, and by using a weight function w(ri), which is maximum at a solder center (ri=0) and is 0 at a maximum radius (ri=r0) for a distance ri from the solder center; and a void evaluation unit for evaluating that the influence of voids is larger as the evaluation function is relatively larger for the each solder.

$$\frac{\sum_{i=1}^{N} w(r_i) p_i}{\sum_{i=1}^{N} w(r_i)} \times 100$$

i: pixel number (1-N)
pi: pixel value (0 or 1)
w(ri): weighting function

The void evaluation apparatus in the solder according to second aspect may further comprise an image extraction unit, which extracts an image in each solder from the two-dimensional X-ray images according to first aspect.

The void evaluation apparatus in the solder according to third aspect may further include a void detection unit, which detects voids for the images in the solder according to first or second aspect.

The void evaluation apparatus in the solder according to fourth aspect, the weighting function w(ri) may be a (r0−ri) in any one of first to third aspects.

A void evaluation method in the solder according to fifth aspect includes:

a step for calculating an evaluation function as shown the following, by using that a pixel value pi contained in the voids is set to 1 and the pixel value pi not contained in the voids is 0 for each pixel constituting an image in the solder, and by using a weight function w(ri), which is maximum at the solder center (ri=0) and is 0 at a maximum radius (ri=r0) for a distance ri from the solder center; and a step for evaluating that the influence of void is larger as a value of the evaluation function is relatively larger for the each solder.

$$\frac{\sum_{i=1}^{N} w(r_i) p_i}{\sum_{i=1}^{N} w(r_i)} \times 100$$

i: pixel number (1-N)
pi: pixel value (0 or 1)
w(ri): weighting function

The void evaluation method in the solder according to sixth aspect may further include the step of extracting an image in each solder from the two-dimensional X-ray images in the above fifth aspecy, and the step of detecting the void portion of images in each solder.

In the void evaluation method in the solder according to seventh aspect, the weighting function w(ri) may be a (r0−ri) in the above fifth or sixth aspect.

The void evaluation computer program according to eighth aspect evaluates voids in the solder, by executing each step of the void evaluation method in the solder to the computer according to any of fifth to seventh aspects.

The computer-readable recording medium according to ninth aspect stores the void evaluation computer program in the solder according to eighth aspect.

(Embodiment 1)

Figure 1:
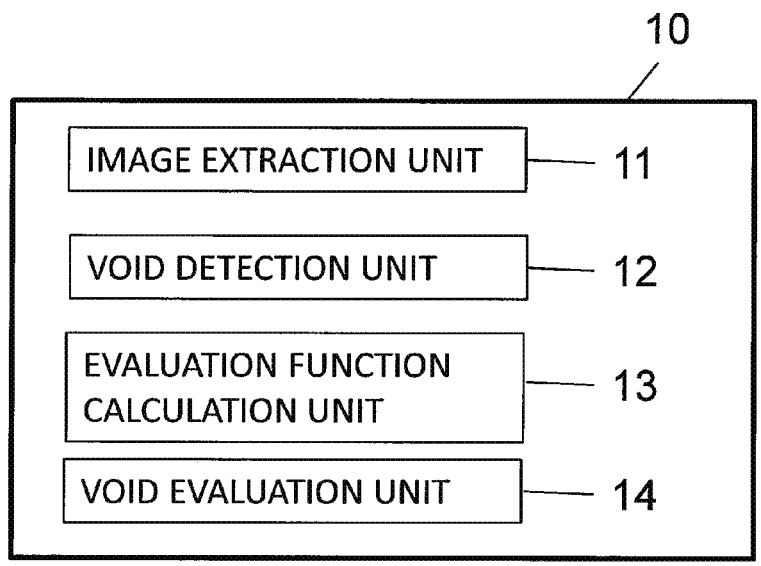
FIG. 1 is a block diagram showing a functional configuration of the void evaluation apparatus in the solder according to the embodiment 1.
Figure 2:
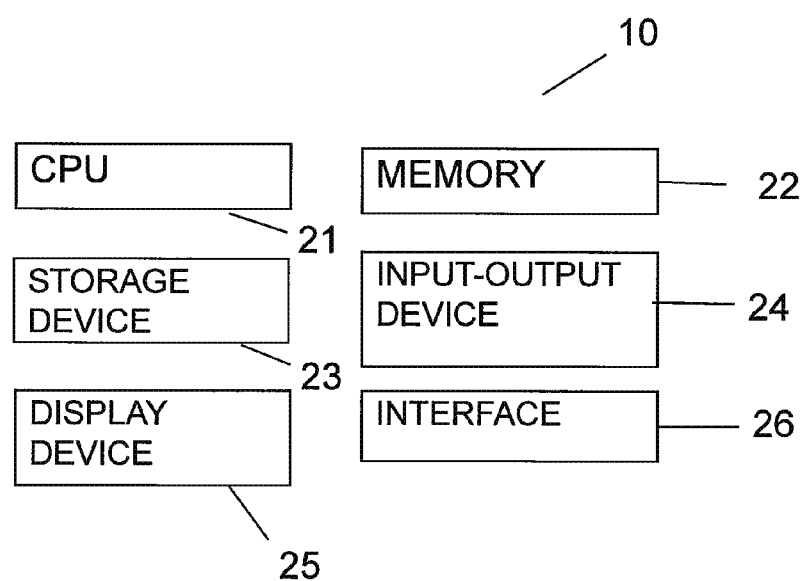
FIG. 2 is a block diagram illustrating a physical configuration of the void evaluation apparatus in the solder according to the embodiment 1.

FIG. 1 is a block diagram showing a functional configuration of the void evaluation apparatus in the solder according to the embodiment 1. FIG. 2 is a block diagram illustrating a physical configuration of the void evaluation apparatus in the solder according to the embodiment 1.

The void evaluation apparatus 10 in this solder includes an evaluation function calculation unit 13 and a void evaluation unit 14 as a functional structure. Incidentally, an image extraction unit 11 and a void detection unit 12 may be included. The image extraction unit 11 extracts the image in the solder from the two-dimensional X-ray images. A void detection unit 12 detects voids of the image in each solder. The evaluation function calculation unit 13 calculates the evaluation function in each solder by using its pixel value and the weighting function w(ri) for each pixel constituting the image in the solder. The void evaluation unit 14 evaluates that the influence of voids is larger as the evaluation function is relatively larger for the each solder.

Further, this void evaluation apparatus 10 in the solder includes CPU 21, memory 22, storage device 23, input-output device 24, the display device 25 and an interface 26 as a physical configuration. That is, this void evaluation apparatus 10 in the solder can be realized by a personal computer, which operates the software for achieving the above-described functional configuration.

(Advantageous Effect)

The void evaluation apparatus in the solder according to the embodiment 1 can perform automatic evaluation of voids in the solder at high speed and adequately.

The influence of voids in actual solder balls, for example, appears as a connection failure because the bonding strength of the solder portion is reduced. It is believed that a crack in the solder occurs by the voids in the solder and the connection failure or the entire apparatus malfunction eventually occurs. The void evaluation apparatus in the solder according to the embodiment 1 can suppress the occurrence of the connection failure at the solder portion.

The following describes the components of the void evaluation apparatus in this solder.

<Image Extraction Unit>

An image extraction unit 11 extracts the image in the solder from the two-dimensional X-ray images. The operation of the image extraction unit 11 will be described below by using FIG. 4 to FIG. 7.

1) Two-dimensional X-ray Images

Figure 4:
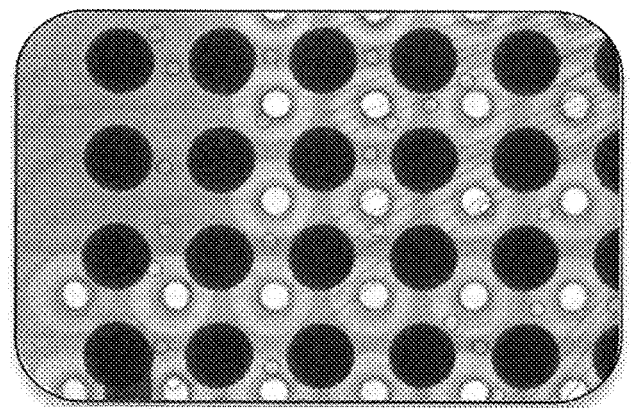
FIG. 4 is an example of the two-dimensional X-ray images.

FIG. 4 is an example of two-dimensional X-ray images. Typical two-dimensional X-ray images, for example, have a bit map format of 0 to 255 gradations. In the two-dimensional X-ray images, the solder balls may often interfere with other substrate members. For example, some of the joint produces a closed solder ball. Therefore, in order to deal with various types of member of the interfering background, it is desirable to use a powerful segment extraction algorithm.

2) Removal of Interfering Member

Figure 5:
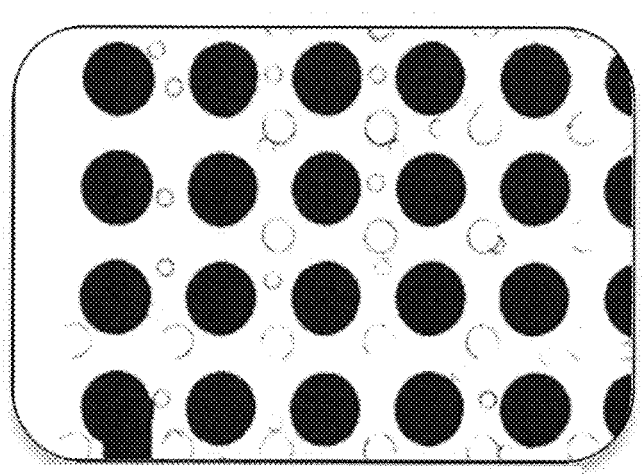
FIG. 5 is an image obtained by removing the effect of interference members of substrate on the basis of the two-dimensional X-ray images in FIG. 4.

FIG. 5 is an image obtained by removing the effect of interference member from the substrate based on the two-dimensional X-ray images in FIG. 4. In this case, by automatically setting the appropriate threshold of strength, the interfering background may be reduced.

3) Circle Detection Corresponding to the Solder Balls

Figure 6:
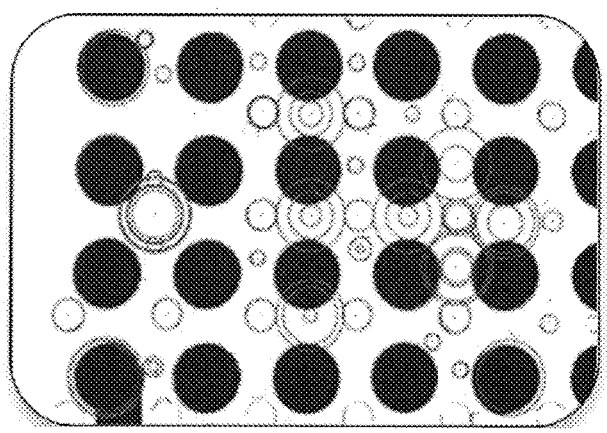
FIG. 6 is an image subjected to a circle detection corresponding to the solder balls on the basis of the image of FIG. 5.

FIG. 6 is an image subjected to a circle detection corresponding to the solder balls on the basis of the image of FIG. 5. Extraction of the possible position of the solder ball may be carried out by using the Hough transform, which is a circle detection algorithm for example. It should be noted that, when large images or dark images are dealt with, the algorithm using the Hough transform may become very slow. Therefore, by performing the circle detection by image resized in place of the original image and reducing the processing amount, the radius value of the circle may be obtained. Further, the circle detection algorithm is not limited to the above Hough transform and it may use other algorithms. Furthermore, when the solder shape of solder ball is such rectangle rather than a circle, other shape matching algorithms may be used.

4) Extraction of Image in Each Solder

Figure 7:
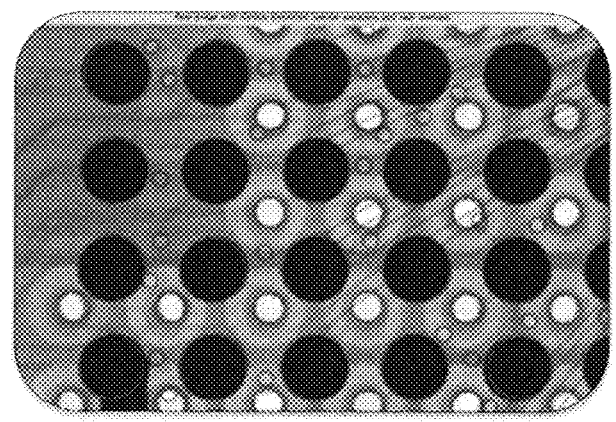
FIG. 7 is an image of the solder balls detected on the basis of the image of FIG. 6.

FIG. 7 is an image of solder balls which are detected based on the image of FIG. 6. To make user-friendly, for example, the default radius range to be applied in the Hough transform may have been spread. As a result, based on the intensity distribution in each ball, the ball not appropriate, that is, the portion that is not a solder ball is eliminated, and the appropriate ball, that is, the portion considered the solder ball is finally selected. By the foregoing description, it is possible to obtain an image in each solder to from the two-dimensional X-ray images.

<Void Detection Unit>

A void detection unit 12 detects voids in the image of each solder. The operation of the void detection unit 12 will be described below by using FIG. 8 to FIG. 17.

1) The Intensity Distribution of the Original Image and the Target Histogram

Figure 8:
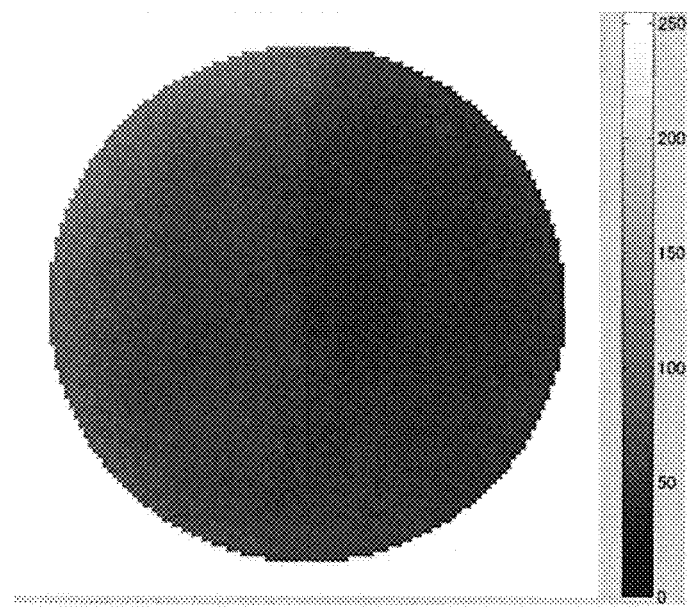
FIG. 8 is an image of a single solder.
Figure 9:
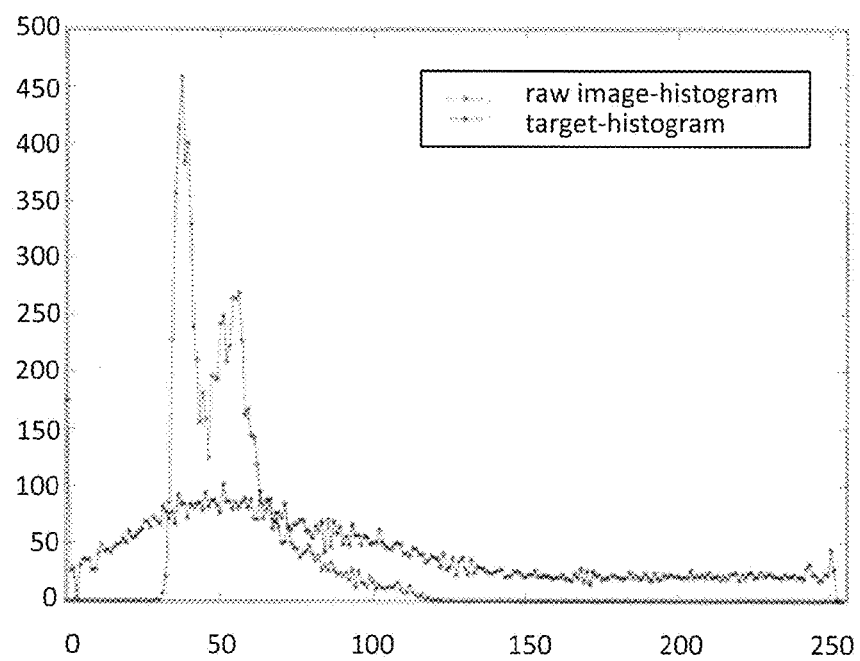
FIG. 9 is a graph showing an intensity histogram and a target histogram of the image of FIG. 8.

FIG. 8 is an image in one solder. FIG. 9 is a graph showing a histogram of intensity, and a target histogram on the image of FIG. 8.

Even if voids in the solder balls appeared bright in the image in one solder, it was actually difficult to detect these voids by various factors. For example, poor image contrasts, irregular shapes produced by a void overlap, the various void size/position and influences of other members are cited as a factor. FIG. 9 shows a target histogram in addition to the histogram of the intensity of the image in the original solder.

Figure 10:
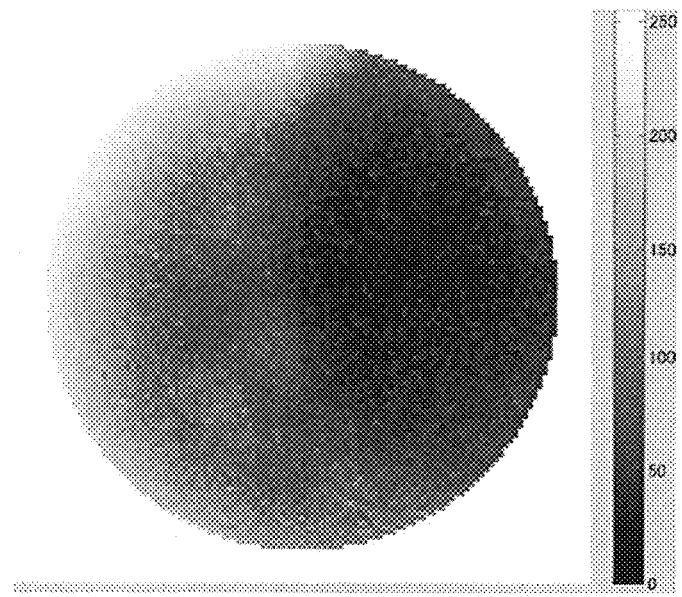
FIG. 10 is an image obtained by enhancing the overall image contrast with a matching histogram equalization method for the image of FIG. 8.
Figure 11:
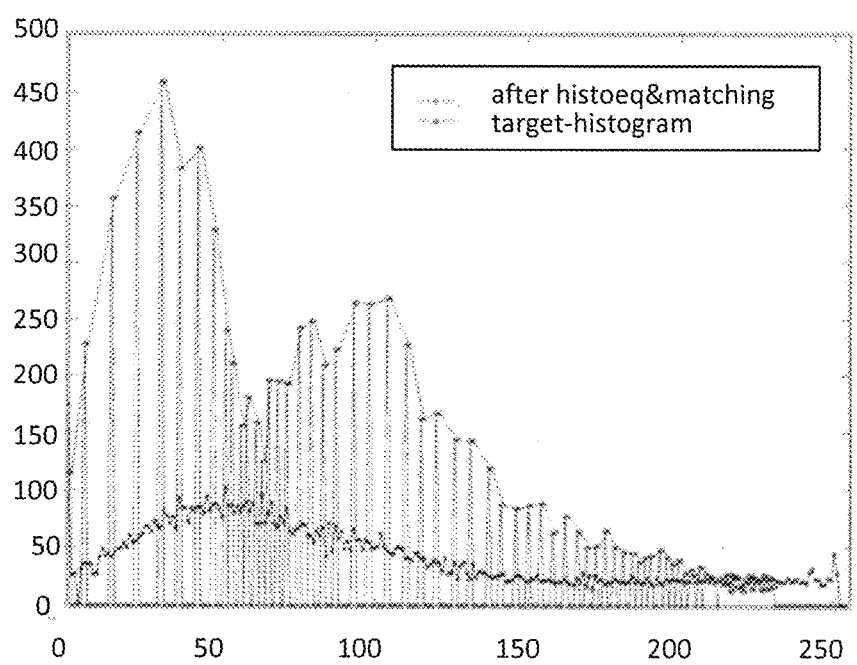
FIG. 11 is a graph showing the intensity histogram and the target histogram of the image of FIG. 10.

2) Enhancement of the Overall Image Contrast by Using a Matching Histogram Equalization Method FIG. 10 is an image obtained by enhancement of the overall image contrast, which uses the matching histogram equalization method for the image of FIG. 8. FIG. 11 is a graph showing a histogram of intensity and a target histogram for the image of FIG. 10.

The quality of the image contrast is changed in accordance with the setting of various data acquisition. Therefore, at first, the conversion of input intensity can enhance the overall image contrast and match the desired target histogram with better contrast a histogram of output intensity.

Figure 12:
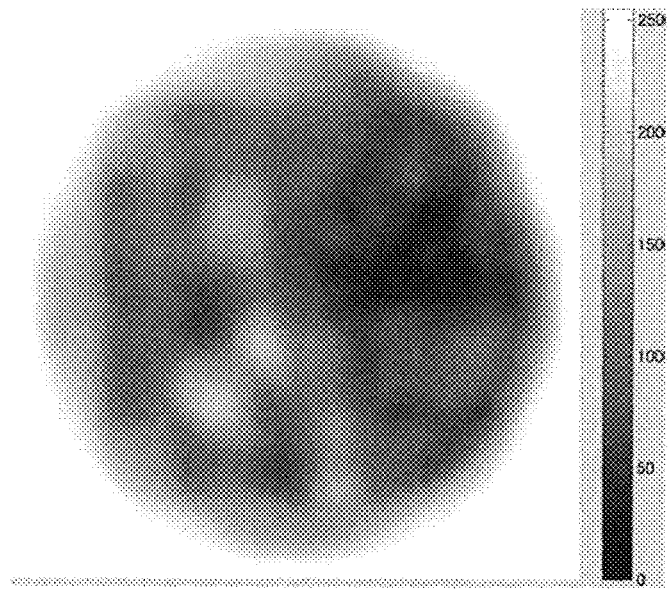
FIG. 12 is an image obtained by enhancing the local contrast with the applicable histogram equalization method for the image in FIG. 10.
Figure 13:
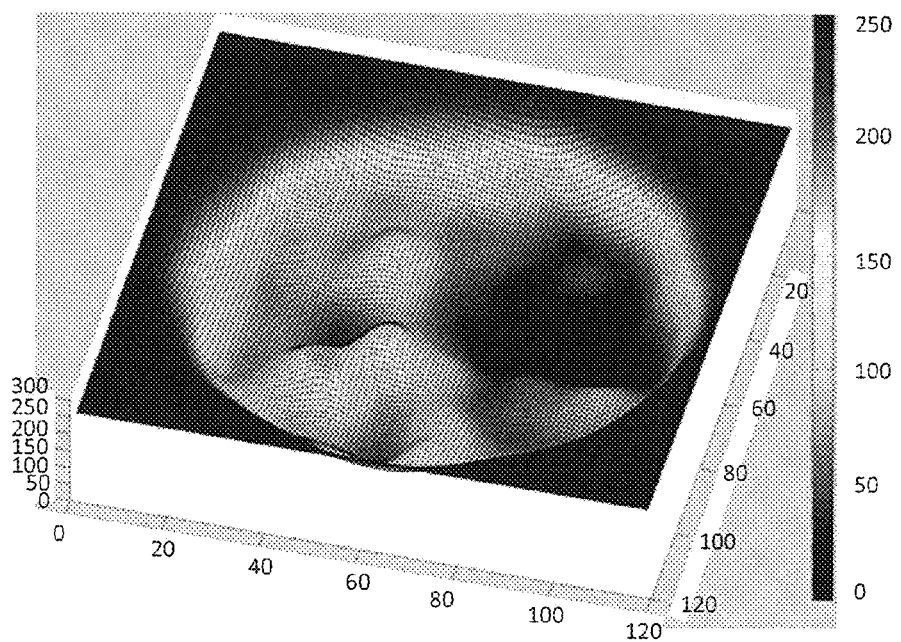
FIG. 13 is an image showing three-dimensionally, which represents the intensity as a depth for the image in FIG. 12.

3) Enhancement of the Local Contrast Using the Applicable Histogram Equalization Method FIG. 12 is an image obtained by enhancing the local contrast using the applicable histogram equalization method on the image of FIG. 10. FIG. 13 is an image showing three-dimensionally the image of FIG. 12, assuming strength as depth.

If the image contrast of the original two-dimensional X-ray images is not good, by CLAHE (Contrast Limited Adaptive Histogram Equalization) after smoothing the images, the local contrast of the local region may be improved. In this case, in order to avoid amplification of noise, it is necessary to control the contrast level.

4) The Discovery of the Boundary between the Concatenated Voids due to the Application of the Water Shedding Algorithm.

Figure 14:
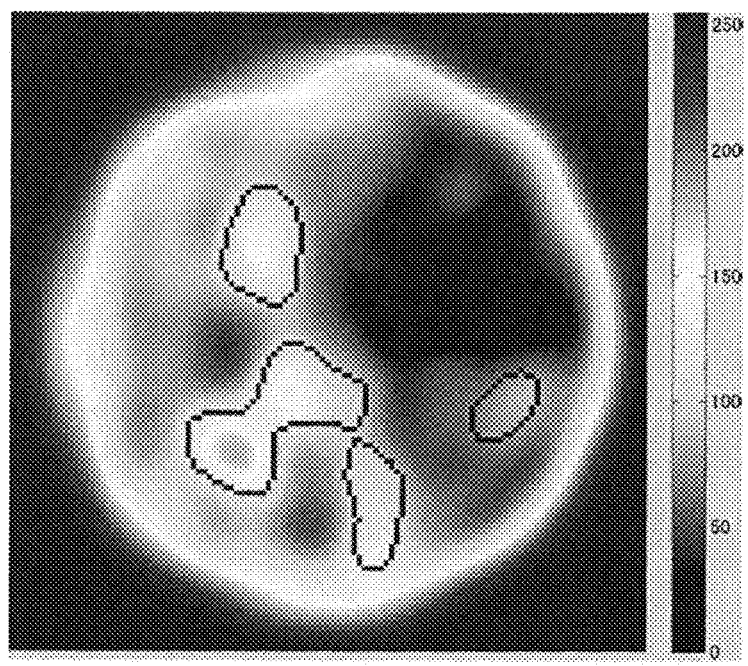
FIG. 14 is an image, wherein the concatenated voids are detected as a single concatenated void accidentally.
Figure 15:
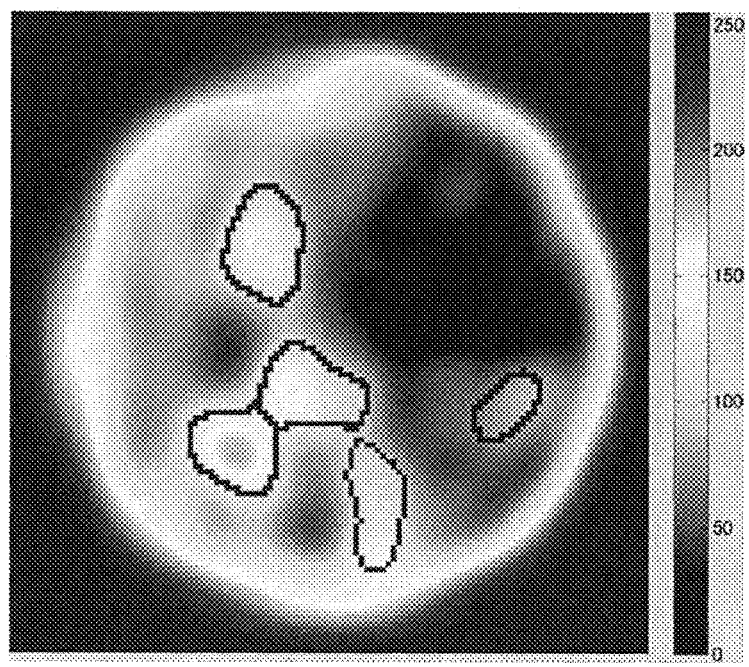
FIG. 15 is an image showing the boundary separating the consecutive voids found by applying a Water shedding algorithm for the image in FIG. 14.

FIG. 14 is an image when concatenated voids are detected as a single concatenated void accidentally. FIG. 15 is a schematic diagram showing a boundary separating a continuous void which is found by application of the Water shedding algorithm.

Boundaries of each void may be effectively determined by applying the Laplacian of Gaussian filter, which detects suitable sizes of the edge. Sometimes continuous voids may be detected as a single concatenated void accidentally. Therefore, it is possible to find the boundaries separating the continuous voids by applying the Water shedding algorithm. Incidentally, the edge detection algorithm is not limited to the above Water shedding algorithm, may be used other algorithms.

5) Complete Separation of Concatenated Voids

Figure 16:
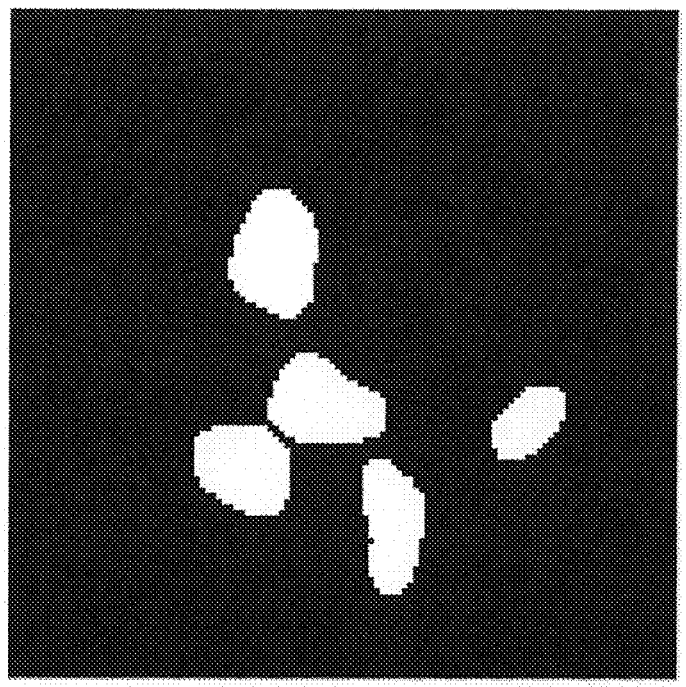
FIG. 16 is a diagram, wherein the voids coupled by extracting only portions of the voids are separated by the boundary for the image of FIG. 15.
Figure 17:
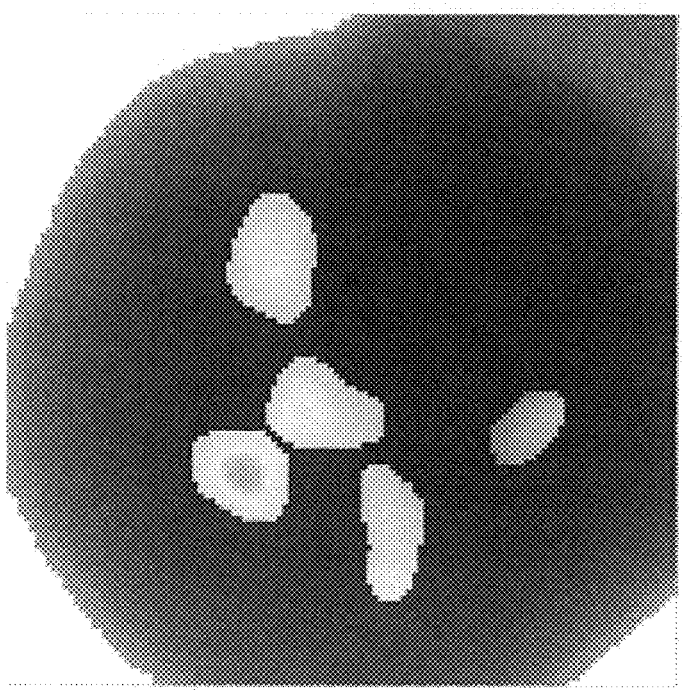
FIG. 17 is an image, which reflects the voids separated in FIG. 16 for the image of FIG. 15.

FIG. 16 is a diagram separated by the boundary from voids coupled by extracting only portions of the voids on the image of FIG. 15. FIG. 17 is an image that reflects the separated voids in FIG. 16 on the image of FIG. 15.

In FIG. 16, two-dimensional X-ray images are performed to be binarized by setting an appropriate threshold and to detect the voids by using Beth numbers, which is the topological information contained in the binary image. Finally, in order to obtain the exact number and area of voids, the concatenated portions are removed by performing a morphological operation and the concatenated voids are completely separated. As above, it detects the portion of voids in each solder.

<Evaluation Function Calculation Unit>

An evaluation function calculation unit 13 calculates a solder evaluation function by using that a pixel value pi contained in the voids is set to 1 and the pixel value pi not contained in the voids is 0 for each pixel constituting an image in the solder, and by using a weight function $w(r_i)$, which is maximum at the solder center ($r_i=0$) and is 0 at a maximum radius ($r_i=r_0$) for a distance $r_i$ from the solder center.

a) The Case of the Weighting of the Pixel-by-pixel Basis

In this case, the evaluation function is defined by the following expression (1).

$$\frac{\sum_{i=1}^{N} w(r_i)p_i}{\sum_{i=1}^{N} w(r_i)} \times 100 \quad (1)$$

i: pixel number (1-N)
ri: distance from the solder center of the i-th pixel
pi: pixel value (0 or 1) of i-th pixel
w(ri): weighting function In the evaluation function of expression (1), i is the pixel number and is from No. 1 to N.

pi is the each pixel value and takes a 0 or 1. Moreover, the weighting function w(ri) may be determined depending on the influence of voids is represented by any function on the distance ri from the BGA center. The present inventors have been led to the present invention by setting the weighting function, wherein the influence is larger as the position of the void is closer to the BGA center and the influence is set as a 0 when it exceeds the maximum radius (r0) of the BGA. For example, weighting function w(ri) may be used as a (r0−ri). The evaluation function in this case is defined by the following expression (2).

$$\frac{\sum_{i=1}^{N} (r_0 - r_i)p_i}{\sum_{i=1}^{N} (r_0 - r_i)} \times 100 \quad (2)$$

Incidentally, the weighting function is not limited to the above case. While the boundary conditions that it is maximum at the BGA center (ri=0) and is 0 at the maximum radius (ri=r0) are satisfied, the weighting function to fit the relation between the evaluation characteristics may be selected. When receiving greater the effect of the distance ri, for example, a quadratic function ((r0−ri)$^2$) or higher order functions or the like may be selected.

b) The Case of the Weighting for Each Void

Also, unlike in the case of each pixel, the evaluation may be performed for each void. In this case, it may be evaluated for each void area Sj. This may be calculated on the assumption that Sj number of pixels at the void center is gathered. In this case, the evaluation function is defined by the following expression (3).

$$\frac{\sum_{j=1}^{M} (r_0 - r_j)S_j}{\sum_{i=1}^{N} (r_0 - r_i)} \times 100 \quad (3)$$

j: void number of (1-M)
rj: distance between the solder center and j-th void center
Sj: area of the j-th void, here expressed as the number of pixels contained in the void.

Here, in the numerator, it is for pixels contained in the void to be processed about the void area Sj for the center of the j-th void rather than individual pixels. In this case, the pixels not contained in the void are not shown in the numerator because the area is treated as 0 in the same manner as described above. On the other hand, the denominator is the expression for all pixels in the same manner as the above expression (2). When dealing with solder balls of a certain size, the denominator may be treated as a constant.

Incidentally, it may be evaluated for each void volume Vj instead of each void area Sj. In this case, the evaluation function is defined by the following expression (4).

$$\frac{\sum_{j=1}^{M} (r_0 - r_j)V_j}{\sum_{i=1}^{N} (r_0 - r_i)} \times 100 \quad (4)$$

j: void number of (1-M)
rj: distance between the solder center and j-th void center
Vj: volume of the j-th void (=4Sj (Sj/π)$^{0.5}$/3, Sj is the area of the void, expressed as the number of pixels contained in the void. Since estimating the volume Vj itself of voids actually may be difficult, the area Sj may be used.

By using the area Sj, the expression (4) is expressed by the following expression (5).

$$\frac{\sum_{j=1}^{M} \frac{4}{3\sqrt{\pi}}(r_0 - r_j)S_j\sqrt{S_j}}{\sum_{i=1}^{N} (r_0 - r_i)} \times 100 \quad (5)$$

The evaluation function is not limited to any shown by the above expressions (1) to (5). The evaluation function may be any one which uses the weight function w(ri), wherein the distance ri from the solder center becomes maximum at the solder center (ri=0) and becomes 0 at the maximum radius (ri=r0). For example, it may be the evaluation function which can evaluate more adequately the effects of two-dimensional/three-dimensional shape of the void.

<Void Evaluation Unit>

A void evaluation unit 14 evaluates that the influence of void is larger as the evaluation function is relatively larger for the each solder.

Figure 18:
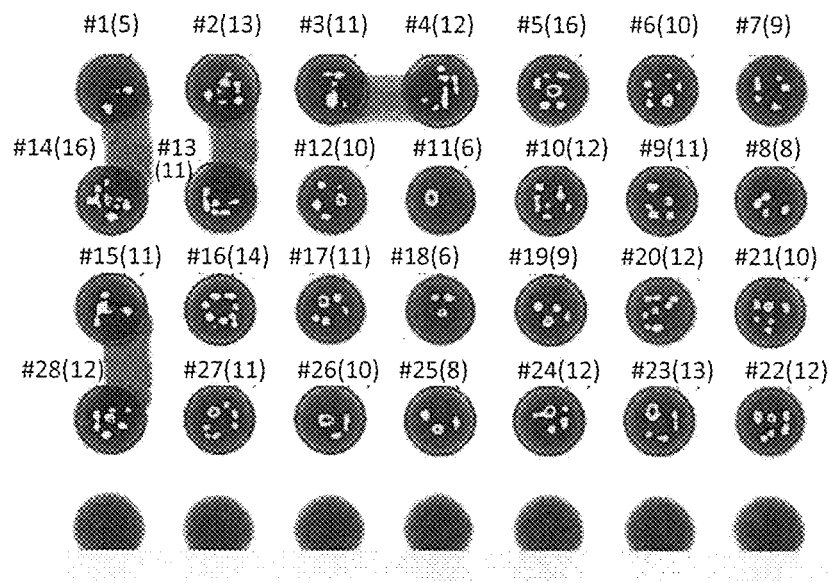
FIG. 18 is an example of an image showing the voids in each solder ball for a plurality of solder balls contained in the two-dimensional X-ray images.
Figure 19:
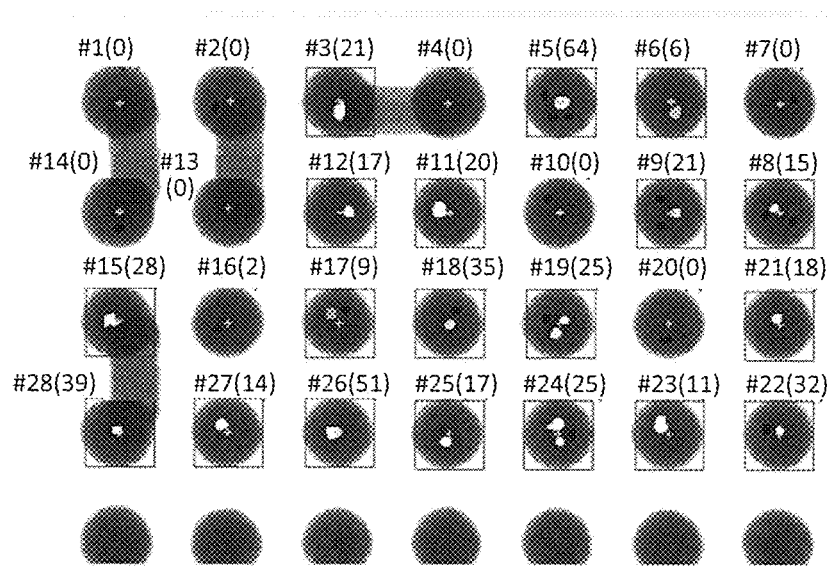
FIG. 19 is an example of an image obtained by performing the set to indicate only voids having relatively large effect.

FIG. 18 is an example of an image showing voids in each solder ball on a plurality of solder balls contained in the two-dimensional X-ray images. FIG. 19 is an example of an image obtained by performing the set to indicate only voids having relatively large effect. FIG. 18 and FIG. 19 are images of each in a plurality of solder balls contained in the two-dimensional X-ray images. The detected void are shown in each solder.

Conventionally, for example, the number of voids and the ratio of the void area to the solder ball area have been used as an indicator of the severity of the influence given by voids in the solder. On the contrary, according to the void evaluation apparatus in the solder on the embodiment 1, the influence of voids in the solder can be evaluated at a high speed and accurately by calculating the evaluation function that uses the weighting function to consider the void with large influence, as compared with the conventional method.

<Void Evaluation Method in the Solder>

In the void evaluation method according to the embodiment 1, it is characterized that the evaluation of voids in the solder is processed by the evaluation function weighted with a weighting function w(ri) for the distance ri from the BGA center of the void.

Figure 3:
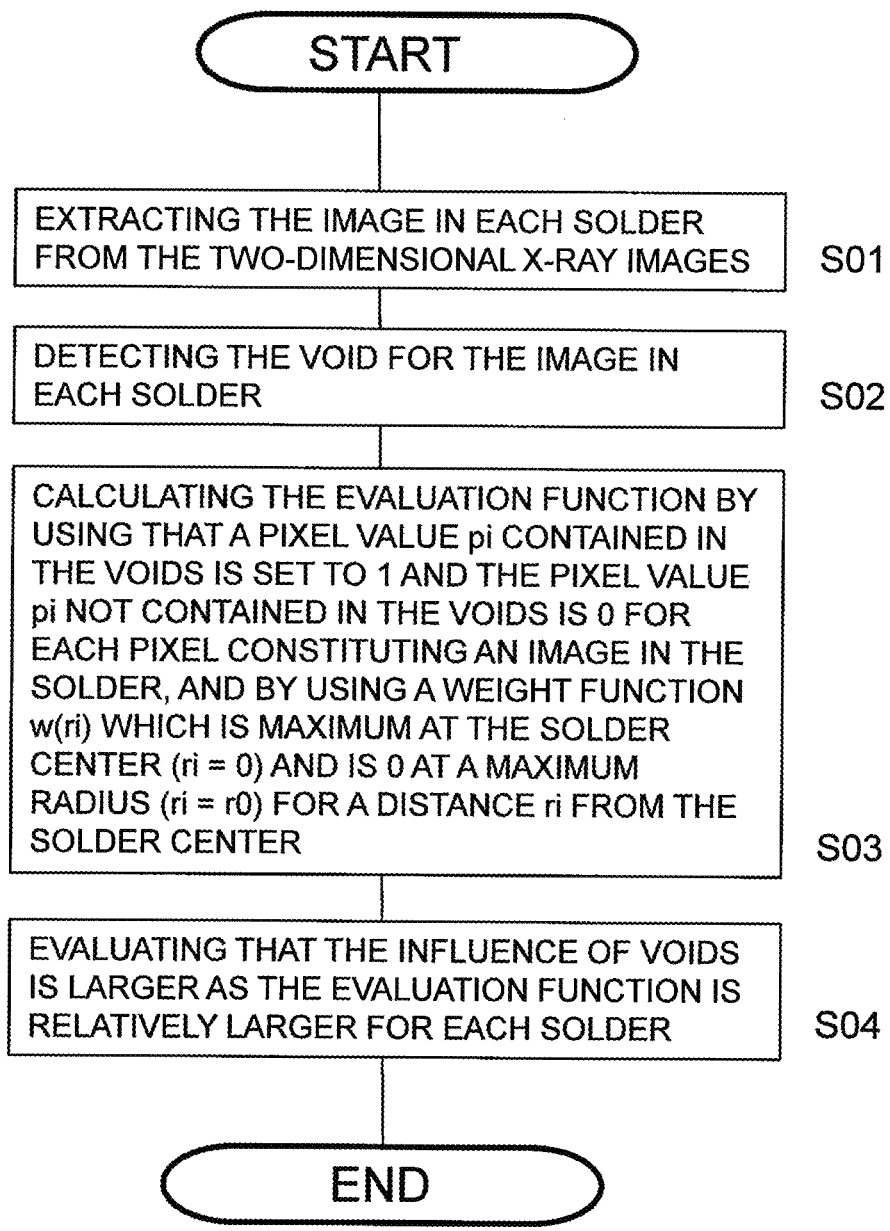
FIG. 3 is a flowchart of the void evaluation method in the solder according to the embodiment 1.

FIG. 3 is a flowchart of a method for evaluating voids in the solder according to the embodiment 1.

The void evaluation method in the solder includes the following steps.

(a) Extracting the image in each solder from the two-dimensional X-ray images (S01).

(b) Detecting the void for the image in each solder (S02).

(c) Calculating the evaluation function by using that a pixel value pi contained in the voids is set to 1 and the pixel value pi not contained in the voids is 0 for each pixel constituting an image in the solder, and by using a weight function w(ri) which is maximum at the solder center (ri=0) and is 0 at a maximum radius (ri=r0) for a distance ri from the solder center (S03).

The evaluation function, for example, is defined by the following expression.

$$\frac{\sum_{i=1}^{N} w(r_i) p_i}{\sum_{i=1}^{N} w(r_i)} \times 100$$

i: pixel number (1-N)
ri: distance from the solder center of the i-th pixel
pi: pixel value (0 or 1) of i-th pixel
w(ri): weighting function (d) Evaluating that the influence of voids is larger as the evaluation function is relatively larger for each solder (S04). By the above steps, the voids in each solder can be automatically evaluated at a high speed and accurately.

(Advantageous Effect)

According to the void evaluation method in the solder concerning the present invention, the automatic evaluation of the voids in the solder can be performed at a high speed and accurately.

<Void Evaluation Computer Program in the Solder>

By executing the steps of the method of evaluating the voids in the solder to a computer, it is possible to be the void evaluation computer program in the solder for performing the evaluation of voids in the solder. Moreover, this void evaluation computer program in the solder may be stored in a computer-readable recording medium. The compute-readable recording medium may be any of the following: a floppy disk, magnetic recording media such as magnetic tape, compact disc (CD), digital versatile disk (DVD), Blu-Ray (registered trademark) disk (BD) or the like of the optical recording medium , a magneto-optical recording medium, USB memory and any of a semiconductor storage medium such as a flash memory.

INDUSTRIAL APPLICABILITY

According to the void evaluation apparatus and the void evaluation method in the solder concerning the present invention, the automatic evaluation of the voids in the solder can be performed at a high speed and accurately. Therefore, the present invention is useful in the evaluation apparatus of the soldered circuit board or the manufacturing apparatus of a semiconductor device including these applications.

DENOTATION OF REFERENCE NUMERALS 10 void evaluation apparatus in the solder
11 image extraction unit
12 void detection unit
13 evaluation function calculation unit
14 void evaluation unit
21 CPU
22 memory
23 storage device
24 input-output device
25 display device
26 interface

The invention claimed is:

1. A void evaluation apparatus in a solder comprising:
an evaluation function calculation unit for calculating a solder evaluation function by using a pixel value pi, contained in the voids, that is set to 1, and a pixel value pi not contained in the voids is 0 for each pixel constituting an image in the solder, and by using a weight function w(ri), which is maximum at a solder center (ri=0) and is 0 at a maximum radius (ri=r0) for a distance ri from the solder center; and
a void evaluation unit for evaluating that influence of voids is larger as the evaluation function is relatively larger for each solder, wherein the void evaluation unit uses the function:

$$\frac{\sum_{i=1}^{N} w(r_i) p_i}{\sum_{i=1}^{N} w(r_i)} \times 100,$$

to obtain images depicting indications of only voids having a relatively large effect, where i is a pixel number (1-N), pi is a pixel value (0 or 1), and w(ri) is the weighting function.

2. The void evaluation apparatus in the solder according to claim 1, further comprising an image extraction unit that extracts an image in each solder from two-dimensional X-ray images.

3. The void evaluation apparatus in the solder according to claim 1, further comprising a void detection unit that detects voids for the images in the solder.

4. The void evaluation apparatus in the solder according to claim 1, wherein the weighting function w (ri) is (r0-ri).

5. A void evaluation method in a solder comprising:
a step for calculating a solder evaluation function, by using a pixel value pi contained in the voids is set to 1 and a pixel value pi not contained in the voids is 0 for each pixel constituting an image in the solder, and by using a weight function w(ri), which is maximum at the solder center (ri=0) and is 0 at the maximum radius (ri=r0) for the distance ri from the solder center; and
a step for evaluating that influence of voids is larger as the value of the evaluation function is relatively larger for each solder, wherein the step for evaluating further comprises the function:

$$\frac{\sum_{i=1}^{N} w(r_i) p_i}{\sum_{i=1}^{N} w(r_i)} \times 100,$$

to obtain images depicting indications of only voids having a relatively large effect, where i is a pixel number (1–N), pi is a pixel value (0 or 1), and w(ri) is the weighting function.

6. The void evaluation method in the solder according to claim 5, further comprising an image extraction step that extracts an image in each solder from the two-dimensional X-ray images; and a void detecting step that detects the voids from images in the solder.

7. The void evaluation method in the solder according to claim 5, wherein the weighting function w (ri) is (r0-ri).

8. The void evaluation method in the solder according to claim 5, wherein each step of the void evaluation method in the solder is executed by a computer, which performs the evaluation of voids in the solder.

9. A computer-readable recording medium, which is stored the void evaluation computer program in the solder according to claim 8.

\* \* \* \* \*